United States Patent [19]

Korisch et al.

[11] Patent Number: 4,770,051

[45] Date of Patent: Sep. 13, 1988

[54] AUTOMATIC SYSTEM FOR ANALYSIS OF GROUND MATERIAL SIZE

[75] Inventors: Semen I. Korisch; Sergei N. Chumak; Petr S. Yasenev, all of Sverdlovsk, U.S.S.R.

[73] Assignee: Uralsky filial Vsesojuznogo nauchno-issledovatelskogo i konstruktorskogo, instituta "Tsvetmetavtomatika", Sverdlovsk, U.S.S.R.

[21] Appl. No.: 933,085

[22] Filed: Nov. 20, 1986

[51] Int. Cl.⁴ ............................................. G01N 15/04
[52] U.S. Cl. ................................................. 73/865.5
[58] Field of Search ................ 73/863.01, 865.5, 61.4, 73/438

[56] References Cited

U.S. PATENT DOCUMENTS

| | | | |
|---|---|---|---|
| 4,175,426 | 11/1979 | Rosenblum | 73/61.4 |
| 4,282,745 | 8/1981 | Burr | 73/61.4 |
| 4,287,757 | 9/1981 | Bucsky et al. | 73/865.5 |
| 4,318,296 | 3/1982 | Parker et al. | 73/61.4 |
| 4,419,879 | 12/1983 | Bush et al. | 73/865.5 |
| 4,588,091 | 5/1986 | Wade | 73/865.5 |

FOREIGN PATENT DOCUMENTS 890157 12/1981 U.S.S.R.
1055998 11/1983 U.S.S.R.

OTHER PUBLICATIONS

Bate et al., "Particle Size Distribution of Particles from 10 to 2000 Microns by Sedimentation Analysis", Analytical Chemistry, vol. 40, No. 2, Feb. 1968.

*Primary Examiner*—Stewart J. Levy
*Assistant Examiner*—Robert R. Raevis
*Attorney, Agent, or Firm*—Lilling & Greenspan

[57] ABSTRACT

An automatic system for analysis of sizes of a ground material includes a sampler for sampling and delivering the ground material in the form of a slurry. A sedimentation of cylinder is provided as is a device for reception of the slurry, its stirring and dosed supply into the sedimentation cylinder. A differential circuit is provided for measuring the mass of the ground material, which did not settle in the sedimentation cylinder as any instant of time during the analysis of the material size including a measuring channel and a correcting channel based on the same LC self-excited oscillator operating in a time sharing mode. An automatic error correction circuit and a data processing and display unit are provided for presenting information on the percentage of solid particles in the sizes being analyzed.

3 Claims, 6 Drawing Sheets

AUTOMATIC SYSTEM FOR ANALYSIS OF GROUND MATERIAL SIZE

BACKGROUND OF THE INVENTION

1. Field of the Invention

The present invention generally relates to measuring instruments and, more particularly, to automatic systems for analysis of particle size distribution of ground materials by a sedimentation technique.

The invention may be used for analysis of the granulometric composition of ground materials at concentration plants in ferrous and nonferrous metallurgy, in chemical industry and other industries producing or using dispersed materials.

2. Description of the Prior Art

Known in the art is an automatic system for analysis of the size of ground materials (USSR Inventor's Certificate No. 890157, IPC GO1 N 15/04, published Dec. 15, 1981) comprising a sedimentation cylinder filled with liquid, a device for sampling and delivery of the ground material in the form of a slurry to the sedimentation cylinder equipped with a sample input unit. The sedimentation cylinder is communicated with a measuring tube, in which the liquid level is measured by means of a level detector whose indications are used for analysis of the granulometric characteristic of the solid particles in the slurry.

However, mechanical destabilizing factors, including shocks, impacts, vibrations of the sedimentation cylinder, which are unavoidable under conditions of a production plant, result in a change in the liquid level in the sedimentation cylinder and the measuring tube and distort the results of the analysis of the ground product size.

Known in the art is an automatic system for analysis of ground material size (USSR Inventor's Certificate No. 1055998, IPC GO1 N 15/04, published Nov. 23, 1983) comprising a sedimentation cylinder filled with liquid and communicating with a measuring tube and a correcting tube, in which the liquid level is converted into an electric signal by means of elements sensing the liquid level. The sedimentation cylinder is provided with a sampling funnel. The liquid level sensing elements are connected through switches to a measuring oscillator with a frequency output. The percentage of solids in the given ground material sizes is determined by the nature of change of the liquid level in the measuring tube with time by a data processing and display unit. The prior art system includes a device for automatic error correction which eliminates the effect of the destabilizing factors on the analysis by monitoring the change of the liquid level in the correcting tube and the change in the time of connection of the liquid level sensing elements to the measuring oscillator. However, the automatic error correction device includes a controlled pulse generator producing pulses whose duration varies under the effect of an analog signal generated by said automatic device. This results in a low noise immunity of the known automatic system which hinders its utilization under conditions of a production plant characterized by a high noise level.

The apparatus, which in its technical essence and in the result obtained, is the closest to the claimed technical solution, is an automatic system for analysis of ground material sizes (U.S. Pat. No. 4,175,426, Int. Cl. GO1 N 15/04, publ. Nov. 29, 1979) comprising a device for sampling and delivery of a ground material in the form of a slurry, a sedimentation cylinder filled with liquid whose density is lower than that of the ground product, said cylinder having a funnel for introducing the ground material, the narrow outlet of said funnel being located within said sedimentation cylinder coaxially therewith; a differential circuit for measuring the mass of the ground material, which did not settle in the sedimentation cylinder at any instant of time of conduction of the ground material size analysis.

The prior art automatic system includes a reference cylinder communicating with the sedimentation cylinder. Both cylinders are identical and have attachments for filling them with a liquid to the same level, two pressure sensing elements located at the same level in bottom portion of the cylinder, a differential pressure sensor, a data processing unit whose data input is connected to the output of said differential pressure sensor while the timer inputs are connected to timer outputs.

The percentage of solid particles within the given sizes is determined by the character of a change with time of the pressure difference on the sensing elements in the reference and sedimentation cylinders after putting the sample into the sedimentation cylinder. However, in the prior art system the introduction of the sample into the sedimentation cylinder is effected directly from the circulating slurry stream. It is well known that in such a stream the particles of different sizes are segregated, i.e. the stream has different density along its length. Therefore, a small sample put into the sedimentation cylinder and localized in the stream does not reflect the granulometric composition of the slurry and is not representative. An increase in the volume of the sample fed into the cylinder is undesirable because it increases the amount of the introduced solid particles causing their hindered sedimentation (mutual influence on the settling speed), conglomeration of the particles and a respective inadmissible increase of the analysis error. The efficiency of the differential circuit is insignificant. This is due to the fact that the pressure sensing elements in the sedimentation and reference cylinders operate in a different way. In the reference cylinder the sensing element is in contact with pure water. In the sedimentation cylinder the pressure sensing element is in contact with solid particles. Therefore, these particles inevitably stick to the pressure sensing element and cause a change in its rigidity with respect to the pressure sensing element in the reference cylinder.

SUMMARY OF THE INVENTION

An object of the present invention is to increase the accuracy of the analysis of the granulometric composition of ground materials.

This object is attained by providing an automatic system for analysis of size fractions of ground material comprising a sampler for sampling and delivery of a ground material in the form of a slurry, a sedimentation cylinder filled with liquid whose density is lower than that of the ground material, said cylinder having a funnel for feeding a required portion (sample) of the ground material, the narrow outlet of said funnel being positioned inside said sedimentation cylinder coaxially therewith; a differential circuit for measuring the mass of the ground material, which have not settled in the sedimentation cylinder, at any instant of time of conduction of the ground material size analysis. According to the invention, the system has a device for receiving the slurry, its stirring and dosed supply into the sedimentation cylinder, said device being connected to said sampler and to the widening part of said funnel of the sedimentation cylinder made in the form of a cylindrical tank accommodating a pressure cup with a propeller mounted on a shaft, while the bottom part of said cylindrical tank is made in the form of a truncated cone provided with a valve. Also provided are an actuator for remote control of supply of liquid into the sedimentation cylinder, an actuator for remote control of the sampling and supply of slurry, an actuator for feeding the sample into the sedimentation cylinder, an actuator for remote control of the removal of waste suspended matter from the sedimentation cylinder, and an actuator for remote control of slurry stirring connected to the propeller shaft. A control device is provided whose control outputs are connected to said actuators for controlling the supply of liquid into the sedimentation cylinder, sampling and delivery of the slurry, introduction of the sample into the sedimentation cylinder, and slurry stirring and removal of the waste suspended matter from the sedimentation cylinder. The sedimentation cylinder is communicated with at least one measuring tube and one correcting tube, which are spaced along the height of said sedimentation cylinder, each of said tubes being secured through its one end to said sedimentation cylinder, while the free ends of said measuring and correcting tubes are located at the same level with respect to the upper end face of the sedimentation cylinder, the end of the narrow branch pipe of said funnel being located in a plane perpendicular to the longitudinal axis of the sedimentation cylinder and extending through the lower point of connection of the fixed end of the correcting tube to the side surface of the sedimentation cylinder or below this plane. Furthermore, the measuring tube is secured below the narrow branch pipe of said funnel; the differential circuit for measuring the mass of the ground materials including measuring and correcting liquid level sensing elements connected respectively to the free ends of the measuring and correcting tubes; switching circuits; a converter for converting the liquid level into an electric signal connected through said switching circuits to said measuring and correcting liquid level sensing elements; an automatic error correction device whose data input is connected to the data output of the converter converting the liquid level into an electric signal, the outputs of the automatic error correction device being connected to the control inputs of the switching circuits and to the control inputs of the converter for converting the liquid level into an electric signal; a data processing and display unit presenting information on the percentage of solid particles in the sizes being analyzed whose data input is connected to the data output of the converter converting the liquid level into an electric signal, the control inputs of said unit being connected to the timer outputs of the control device whose clock-pulse and count-pulse outputs are connected respectively to the clock-pulse and count-pulse inputs of said automatic error correction device.

The automatic error correction device may include a scaler whose input is connected to the output of the converter for converting the liquid level into an electric signal, a first trigger whose first input is connected to the output of the scaler while the output is a first output of the automatic error correction device, a counting flip-flop trigger whose input is connected to the clock input of the control device while the direct output is connected to the second input of the first trigger, a second trigger whose output is a second output of the automatic error correction device, while the first input is connected to the inverse output of the counting trigger. Also provided are a reversible counter and direct and inverse count switching circuits, the signal inputs of the direct and inverse count switching circuits being interconnected and connected to the counting pulse input of the control device, the output of the direct count switching circuit being connected to the adding input of said reversible counter, the output of the inverse count switching circuit being connected to the substracting input of the reversible counter whose output is connected to the second input of the second trigger, while the control inputs of the direct and inverse count switching circuits being connected to the outputs of the first and second triggers respectively.

The automatic system for analysis of ground material size fractions makes it possible to improve the representativeness of the sample with respect to the process flow of ground material being measured while avoiding a methodical error in the analysis caused by hindered sedimentation of solid particles in the sample. For this purpose, a considerable amount of slurry is taken from the process flow of ground materials and a small sample taken from the selected slurry is fed into the sedimentation cylinder, said sample completely preserving all properties of the selected slurry due to its intensive stirring.

The efficiency of the differential circuit for measuring the mass of the non-settled solid particles in the sedimentation cylinder at any instant of conducting the analysis is increased due to complete identity of operation of the liquid level sensing elements none of which is in contact with the slurry.

In addition, the automatic error correction circuit does not comprise elements producing analog signals or controlled by analog signals. This provides a high accuracy of the analysis of the ground material sizes under complex industrial conditions characterized by a high level of electromagnetic noise.

BRIEF DESCRIPTION OF THE DRAWINGS

The invention is further described by way of example with reference to the accompanying drawings, in which.

A PREFERRED EMBODIMENT OF THE INVENTION

The automatic system for analysis of ground material size fractions comprises a sampler 1 (FIG. 1) for sampling and delivering ground materials in the form of a slurry, a sedimentation cylinder 2 with a funnel 3 filled with liquid 4 whose density is lower than that of the ground material 5. The end face 6 of a narrow branch pipe 7 of the funnel 3 is located inside the sedimentation cylinder 2. The funnel 3 is used for feeding a required portion of a ground material 5 (sample).

Figure 1:
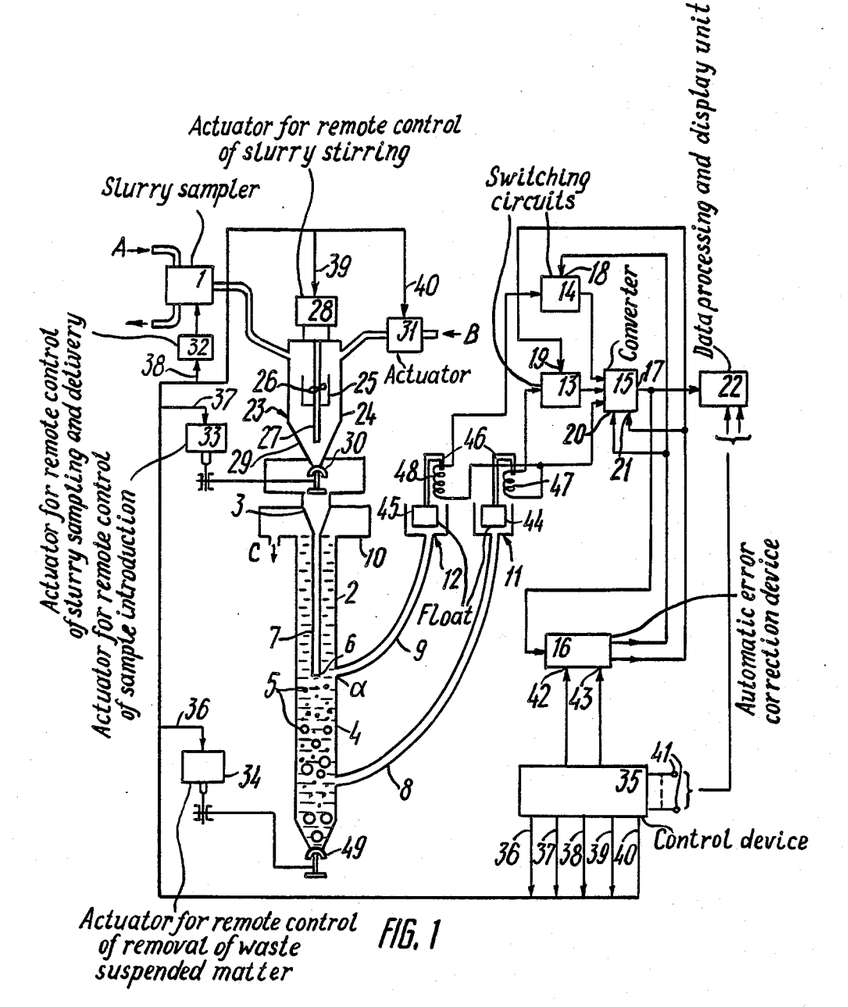
FIG. 1 is a block diagram of the automatic system for analysis of ground material size fractions, according to the invention.

The sedimentation cylinder 2 is communicated with a measuring tube 8 and with a correcting tube 9 spaced along the height of the sedimentation cylinder 2. Each tube 8, 9 has one fixable end secured to the sedimentation cylinder 2, while the free ends of the tubes 8, 9 are placed at the same level with respect to the upper end face 10 of the sedimentation cylinder 2, said end face 6 of the narrow branch pipe 7 of the funnel 3 in this embodiment being arranged in a plane perpendicular to the longitudinal axis of said sedimentation cylinder 2 and extends through the lower point α of connection of the fixable end of the correcting tube 9 with the side surface of the sedimentation cylinder 2.

The automatic system also comprises a differential circuit for measuring the mass of the ground material 5 which has not settled in the sedimentation cylinder 2 at any instant of time during the analysis, the differential circuit including a measuring liquid level sensing element 11 and a correcting liquid level sensing element 12 connected to the free ends of the tubes 8, 9, switching circuits 13, 14, and a converter 15 for converting the liquid level into an electric signal. The converter 15 is connected to the sensing elements 11, 12 through the switching circuits 13, 14. The outputs of the switching circuits 13, 14 are connected respectively to the measuring and correcting inputs of the converter 15.

The measuring tube 8, measuring sensing element 11 and switching circuit 13 form a measuring channel.

The correcting tube 9, correcting sensing element 12 and switching circuit 14 form an error correction channel.

The differential circuit also includes an automatic error correction device 16 whose data output is connected to a data input 17 of the converter 15. The outputs of the automatic error correction device 16 are connected to the control inputs 18 and 19 of the switching circuits 13, 14 respectively and to the control inputs 20, 21 of the converter 15.

The differential circuit also comprises a data processing and display unit 22 presenting information on the percentage of solid particles in the sizes being analyzed. The data input of the unit 22 is connected to the data output 17 of the converter 15. The data processing and display unit 22 may be based on any prior art computer, e.g. that used in U.S. Pat. No.4,175,426.

In addition, the automatic system includes a device 23 for reception of the slurry, stirring it and feeding it into the sedimentation cylinder 2. The device 23 is connected to the sampler 1 (FIG. 1) for sampling and supplying ground materials and to the widening part of the funnel 3 of the sedimentation cylinder 2.

The device 23 is made in the form of a cylindrical tank 24 accommodating a pressure housing 25 with a propeller 26 mounted on a shaft 27 connected to an actuator 28 for remote control of slurry stirring. The bottom portion 29 of the tank 24 is made in the form of a truncated cone equipped with a valve 30.

Furthermore, the automatic system comprises an actuator 31 for remote control of the supply of liquid into the sedimentation cylinder 2 (in FIG. 1 the direction of liquid is shown by an arrow B), an actuator 32 for remote control of the slurry sampling and delivery (in the figure the slurry is fed in the direction shown by the arrow A), an actuator 33 for remote control of the supply of the slurry into the sedimentation cylinder 2, and an actuator 34 for remote control of the removal of the waste suspended matter from the sedimentation cylinder 2.

The automatic system includes a control device 35 whose control outputs are connected via circuits 36, 37, 38, 39, 40 to the actuators 34, 33, 32, 28 and 31 respectively.

The control inputs of the unit 22 are connected to the timer outputs 41 of the control device 35, and the clock and counting pulses outputs of the device 35 are connected to the inputs 42, 43 of clock and counting pulses of the device 16. The sensing elements 11, 12 include floats 44, 45 connected to cores 46 which cooperate with coils 47, 48. One point of connection of the coils 47, 48 is connected to the common input of the converter 15. The bottom part of the sedimentation cylinder 2 is equipped with a valve 49.

The actuator 32 is connected to the sampler 1, the actuator 33 is connected to the valve 30, and the actuator 34 is connected to the valve 49.

The automatic error correction device 16 comprises a scaler 50 (FIG. 2) whose input is connected to the data output 17 (FIG. 1) of the converter 15, a trigger 51 (FIG. 2) whose first input is connected to the output of the scaler 50, while the output is a first output of the automatic error correction device 16, a counting trigger 52 whose input is a clock input 42 of the device 16 while the direct output 53 is connected to the second input of the trigger 51, a trigger 54 whose output is a second output of the device 16, while the first input is connected to the inverse output 55 of the counting trigger 52, a reversible counter 56 and direct and inverse count switching circuits 57 and 58 respectively. The signal inputs of the switching circuits 57, 58 are interconnected and serve as a counting input 43 of the automatic error correction device 16. The output of the switching circuit 57 is connected to the summing input of the reversible counter 56, while the output of the switching circuit 58 is connected to the subtracting input of the reversible counter 56. The output of the reversible counter 56 is connected to the second input of the trigger 54, the control inputs of the switching circuits 57 and 58 are connected to the outputs of the triggers 51 and 54 respectively. Other embodiments of the automatic error correction device 16 are possible.

The converter 15 for converting the liquid level into an electric signal is shown in the form of an LC self-excited oscillator and includes transistors 59 (FIG. 3), 60, the base of the transistor 59 being connected to the collector of the transistor 60, while the collector of the transistor 59 is connected to the junction of the coils 47, 48, to which are connected series capacitors 61, 62, the second output of the capacitor 62 being connected to the common point of the circuit. The common point of the capacitors 61, 62 is connected to the base of the transistor 60. The converter 15 includes resistors 63, 64 connected in series, the common point of the resistors 63, 64 being connected to the base of the transistor 60, while the other outputs of these resistors are connected respectively to the power supply bus and to the common point of the circuit. The emitter of the transistor 60 is a data output 17 of the converter 15 and is connected via a resistor 65 to the common point of the circuit.

Figure 3:
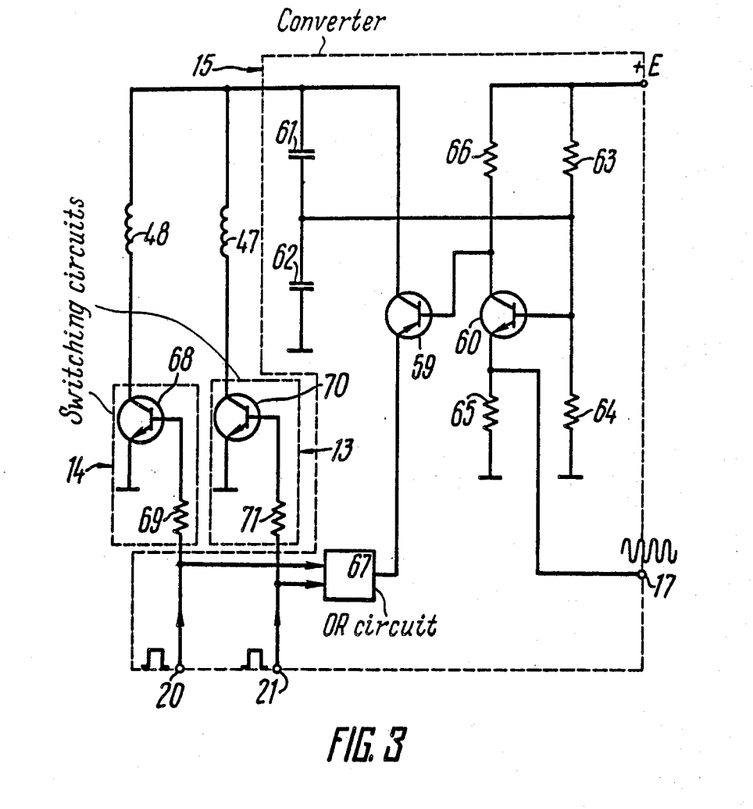
FIG. 3 is a schematic diagram of the converter for converting a liquid level into an electric signal made in the form of an LC self-excited oscillator with a frequency output, according to the invention.

The collector of the transistor 60 is connected to the power supply bus through a resistor 66.

The converter 15 includes an OR circuit 67 whose inputs are control inputs 20, 21 of the converter 15, while the output is connected to the emitter of the transistor 59.

The switching circuit 14 is made in the form of a transistor 68, to the base of which is connected one end of a resistor 69 whose second end is connected to the control input 20 of the converter 15. The switching circuit 13 is made in the form of a transistor 70, to the base of which is connected one end of a resistor 71 whose second end is connected to the control input 21 of the converter 15. The collectors of the transistors 68, 70 are connected to the outputs of the coils 48, 47 respectively, the emitters of the transistors 68, 70 being connected to the common point of the system.

The control device 35 includes a reference signal generator 72 (FIG. 4), a timer 73 whose input is connected to the output of the reference signal generator 72, the outputs of the timer 73 being a timer output 41 of the control device 35.

Figure 4:
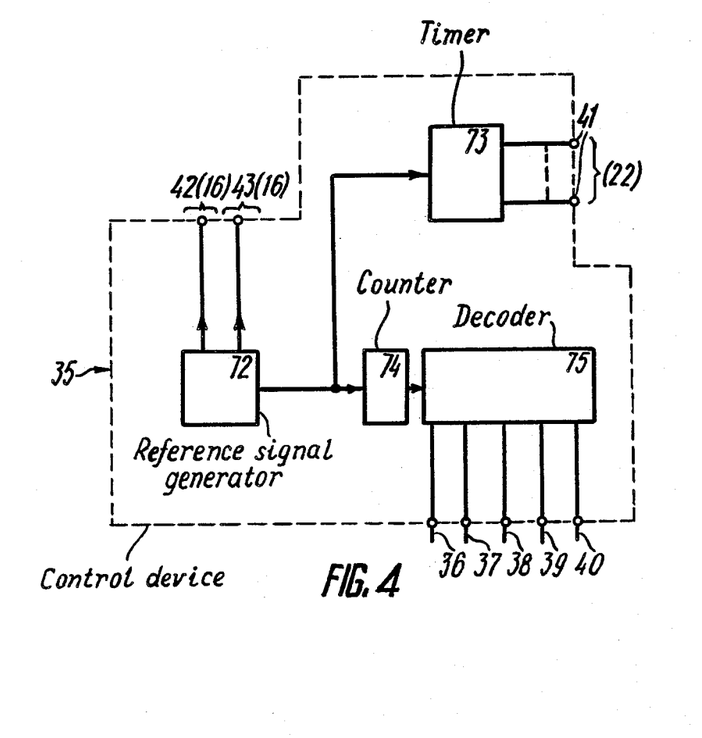
FIG. 4 is a block diagram of the control device, according to the invention.

The control device 35 also includes a counter 74 and a decoder 75, the input of the counter 74 being connected to a output of the reference signal generator 72, while the output of the counter 74 is connected to the input of the decoder 75 whose outputs are connected to the circuits 36, 37, 38, 39, 40. The clock and counting outputs of the reference signal generator 72 are clock and counting outputs of the control device 35.

The automatic system for analysis of ground material size fractions operates as follows.

The sampler 1 (FIG. 1) for sampling and supplying ground materials by commands sent by the control device 35 during a selected time interval samples and stores the slurry taken from the process flow A. After a preset time interval the slurry is fed into the device 23 which effects reception, stirring and small portion delivery of the sample into the sedimentation cylinder 2. In the device 23 the slurry is thoroughly stirred to provide it with a uniform density throughout the whole volume. This is obtained by turbulizing the slurry by means of the propeller 26 mounted inside the pressure housing 25. The pressure drop produced between the end faces of the pressure housing during the rotation of the shaft 27 connected to the actuator 28 provides intensive agitation of the slurry. The slurry is stirred so that any volume inside the device represents the whole volume of the slurry being analyzed. Then a valve 30 opens and a small portion of the slurry is fed through the funnel 3 into the sedimentation cylinder 2 preliminarily filled with liquid.

Depending on what is the finest size of the material being analyzed, the granulometric analysis time is changed, while the period of feeding the sample for the analysis must be not shorter than the time of analysis of the finest particles. The control device 35 sends commands for sampling and preparation of the slurry for analysis and controls the time of recording the data which are then stored in the data processing and display unit 22.

In order to provide high-accuracy analysis of the sample sizes, the sample must be fed into the sedimentation cylinder 2 impulse-like. This means that the time between the beginning and end of delivery of the sample into the cylinder must be minimum so that, as far as possible, settling of the particles in the front and rear parts of the sample starts simultaneously, otherwise a space shift appears between the particles of the same size, which would distort the results of the measurement. The time of opening the valve 30 must be tenths of one second. In this case we practically eliminate both the time shift and segregation (accumulation of separation) of the particles in the sample being fed. Making of the bottom portion of the tank 24 in the form of a truncated cone provides a considerable speed of the sample and passage of a required amount of material into the sedimentation cylinder 2 during a short time. Since this speed is practically the same for all particles, it is taken into account when calibrating the automatic system for analysis of ground material size fractions.

Thus a large volume of slurry is taken from the process flow and fed into the device 23, which very accurately represents the granulometric composition of the flow. At the same time, the sedimentation cylinder 2 is supplied with a small sample of the slurry, which also represents the process flow being measured.

The introduction of a small sample of the slurry due to short-time opening of the valve 30 eliminates hindered sedimentation of the particles, i.e. excludes the main methodical error in the analysis.

The liquid level in the measuring tube 8 represents the mass of solid particles that did not settle in the sedimentation cylinder 2 at any instant of time of conduction of the analysis. A change of the liquid level in the measuring tube 8 presents data on the particle size distribution of the slurry introduced for the analysis if hindered sedimentation of particles does not take place. This condition is fulfilled by introducing a small amount of slurry into the sedimentation cylinder 2. The liquid level in the correcting tube 9 is not associated with the amount of solid particles introduced into the sedimentation cylinder 2. A change of this level is caused by destablizing factors: shocks, impacts, and vibrations. This change is used for correcting the errors of the analysis of the sizes caused by the destabilizing factors. The information on the levels in the tubes 8 and 9 is then converted into electric signals by means of the liquid level sensing elements 11 and 12 and the converter 15.

The data fed from the converter 15 are processed by the unit 22. This processing results in finding the weight percentage of size fractions and this is the output data of the automatic system. The obtained results of the analysis of the ground material sizes are used for controlling the granulometric composition of solid particles in the process flow.

Figure 5:
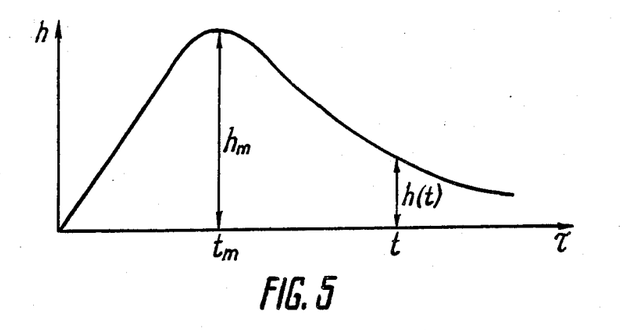
FIG. 5 is a graph illustrating a time-dependant change of the increase in the liquid level in the measuring tube, according to the invention.

The solid particles fed into the sedimentation cylinder 2 occupy the space between the measuring tube 8 and the correcting tube 9, because the end face 6 of the outlet 7 of the funnel 3 is located in the plane perpendicular to the longitudinal axis of the sedimentation cylinder 2 and extends through the lower point of connection of the fixable end of the correcting tube 9 to the side surface of the sedimentation cylinder 2. Therefore, the liquid levels in the correcting tube 9 and the upper portion of the sedimentation cylinder 2 are the same (initial levels), while the liquid level in the measuring tube 8 overcomes the initial level by an increment $h_m$ (FIG. 5). This value is calculated as follows.

The solid particles introduced into the sedimentation cylinder 2 exert a pressure on the liquid located above the inlet of the measuring tube 8, said pressure being expressed by $$P = \frac{F_1}{S} = \frac{V_1(\rho_1 - \rho_2)}{S} \quad (1)$$

where $F_1$ is the resultant force action on the particles and equal to the difference between the force of gravity and the buoyancy;

S is the cross-sectional area of the sedimentation cylinder 2;

$V_1$ is the volume occupied by the solid particles in the sample introduced into the sedimentation cylinder 2;

g is the free fall acceleration; $\rho_1$, $\rho_2$ are the densities of the solid particles and the liquid respectively.

Under the effect of this pressure the liquid level in the measuring tube 8 rises for a value $$h_m = \frac{P}{g\rho_2} \quad (2)$$

Having substituted (1) into (2) and replacing $$V_1 = \frac{m_o}{\rho_1} \quad (3)$$

where $m_o$ is the mass of introduced solid particles, we obtain an expression for $h_m$ $$h_m = \frac{m_o(\rho_1 - \rho_2)}{S\rho_1\rho_2} = Dm_o \quad (4)$$

where D is the proportionality factor.

From expression (4) it follows that the liquid level in the measuring tube 8 at any instant of time is proportional to the mass of solid particles, which did not settle below the level of connection of the measuring tube 8 and the sedimentation cylinder 2

$$h(t) = Dm(t), \quad (5)$$

where h(t) is the increment of the liquid level in the measuring tube 8 at the instant t; m(t) is the weight of particles remaining suspended at the instant t during the analysis (weight of the size fraction "d")

The percentage of the solid particles of the size "−d" is determined by the formula:

$$\delta_{-d} = \frac{m(t)}{m_o} \cdot 100 \quad (6)$$

Having substituted in (6) expressions (4) and (5), we obtain the algorithm of definition of the weight percent of solid particles of an arbitrary size "−d"

$$\delta_{-d} = \frac{h(t)}{h_m} \quad (7)$$

The instants of time t of settling of solid particles having an arbitrary diameter "d" are calculated according to the Stocks formula using the sedimentation cylinder height. These instants of time "t" can be later made more accurate experimentally when calibrating the system.

After the sample has been introduced into the sedimentation cylinder 2, the liquid level in the measuring tube 8 (FIG. 1) is increased attaining the maximum increment $h_m$ at the instant $t_m$ (FIG. 5). The float-type measuring sensing element 11 (FIG. 1) converts the liquid level variation into a change of the inductance of a coil 47 connected through the switching circuits 13, 14 to the oscillatory circuit of the converter 15 converting the liquid level into electric signals.

The information parameter of the converter 15 is the frequency of electric oscillations. The LC self-excited oscillator based on transistors 59 (FIG. 3) and 60 generates wave trains (radio pulses). The number of oscillations (waves) in the train is proportional to the increment of the liquid level in the measuring tube 8 (FIG. 1). The wave trains are applied to the data input of the data processing and display unit 22 in which the number of waves in the train is calculated, the maximum level $h_m$ is recorded (for example by analyzing the sign of steepness of the liquid level in the measuring tube 8, as are the values of the level at the instant t (FIG. 5) corresponding to the size selected for the analysis. Then the weight percentage of solid particles of the given size is calculated by formula (7) and this information is presented on a display.

The number of pulses in the train is determined by the formula $$N(t) = F(t)T, \quad (8)$$

were F(t) is the current value of the frequency of oscillation of the LC self-excited oscillator at the instant T;

T is the duration of the wave train.

From expression (8) it follows that the value N(t), which is a data parameter, depends not only on the frequency of oscillations F(t) but also on the duration T of the wave train. Expression (8) is used for automatic correction of the analysis errors.

In the process of operation the system can be subjected to the effect of various mechanical and electric destabilizing factors. The destabilizing mechanical factors result in a change of the initial liquid level in the measuring tube 8 (FIG. 1). These factors include shocks, impacts and vibration, which are unavoidable under industrial conditions, and can cause splashing out of liquid from the sedimentation cylinder 2. Since small samples are introduced to provide free settling of the solid particles, the useful changes of the liquid level in the measuring tube 8 are low: as a rule they are equal to 5-7 mm. The change of the liquid level under the effect of destabilizing factors can reach 2-3 mm and this may cause a considerable error when performing the measurements.

The instability of the initial liquid level in the sedimentation cylinder 2 is also caused by different density of the slurry fed for the analysis. When the sedimentation cylinder 2 is being prepared for operation, it is filled with liquid to its upper end face 10. The liquid level in the sedimentation cylinder 2 cannot be higher due to the overflow effected in the direction of the arrow C. However, the liquid level in the sedimentation cylinder 2 varies within a wide range after the sample has been fed into this cylinder, because the volume of the overflown liquid depends on the kinetic energy of the sample and this energy depends on the density of the slurry being analyzed.

The electrical destabilizing factors include changes of the parameters of the oscillatory circuit as a result of changes in temperature, humidity, ageing of components resulting in the frequency fluctuation of the LC self-excited oscillator. The effect of the destabilizing factors on the process of analysis is eliminated by the automatic error correction device 16.

Figure 2:
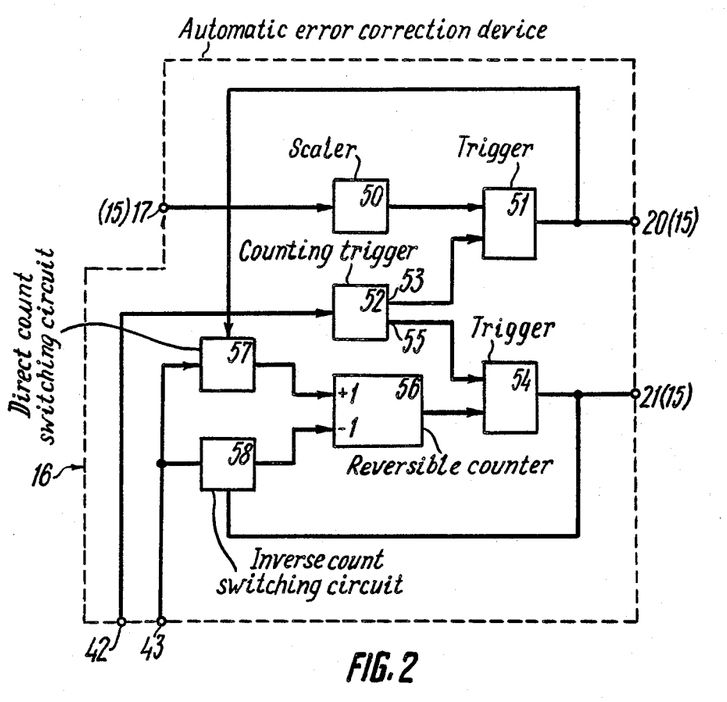
FIG. 2 is a functional diagram of the automatic error correction device, according to the invention.
Figure 6A:
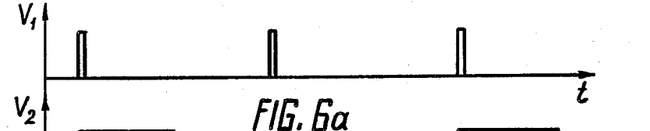
FIGS. 6a–6e time diagrams illustrating the operation of the measuring and correcting channels of the automatic system in the time sharing mode, according to the invention.
Figures 6B, 6C:
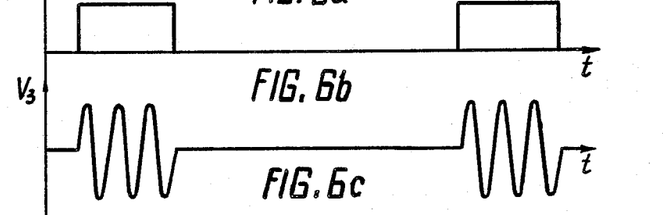

The clock pulses $V_1$ (FIG. 6a) are applied to the input of the counting trigger 52 (FIG. 2). From the direct output 53 the front edge of the voltage pulse $V_2$ (FIG. 6b) transmits a short command for setting the trigger 51 (FIG. 2) to the "one" state. The high potential appearing at the "one" output of the trigger 51 renders the switching circuit 14 (FIG. 1) conductive and a correction coil 48 is connected to tuned circuit of the LC self-excited oscillator built around transistors 59, 60. The self-excited oscillator generates a corrective train of oscillations $V_2$ (FIG. 6c) whose duration is in generally variable and includes a number of waves equal to the scale factor of the scaler 50 (FIG. 2) (for example, $N_1=1000$ waves). The duration $T_1$ of the correcting wave train is determined by the formula $$T_1 = \frac{N}{f_1} \tag{9}$$

where $f_1$ if the frequency of oscillation of the LC self-excited oscillator with a correcting coil 48.;

$N_1$ is the selected (fixed) number of waves in the correcting train (scale factor).

The automatic system is calibrated with a fixed value of the liquid level on the sedimentation cylinder 2. In this case the correcting channel frequency is equal to $f_{01}$, while the duration of the wave train is found from the expression $$T_{01} = \frac{N_1}{f_{01}} \tag{10}$$

If the liquid level in the sedimentation cylinder 2 drops down, the core 46 (FIG. 1) of the correcting liquid level sensing element 12 enters the coil 48 whose inductance increases, while the frequency at the output of the LC self-excited oscillator decreases. The duration of the correcting wave train, which, as before, includes $N_1$ waves, increases. In a general case the duration of the correcting wave train us determined by the expression $$T_1 = \frac{N_1}{f_{01} + \Delta f_1} = \frac{N_1}{f_{01}\left(1 + \frac{\Delta f_1}{f_{01}}\right)} = \frac{T_{01}}{\left(1 + \frac{\Delta f_{01}}{f_{01}}\right)} \tag{11}$$

where $\Delta f_1$ is the variation of the frequency of the LC self-excited oscillator with a correcting coil 48 due to the effect of the destabilizing factors.

After $N_1$ waves have passed through the scaler 50 (FIG. 2), the latter produces an output pulse resetting the trigger 51 to the "zero" state. The switching circuit 14 is rendered nonconductive and the correcting wave train $V_3$ (FIG. 6c) is ceased.

The time interval (duration) $T_1$ is coded in a binary code, stored and then is used during the operation of the measuring channel. For this purpose, simultaneously with switching of the correcting channel, the trigger 51 (FIG. 2) renders the switching circuit 57 conductive and the count pulses are applied to the direct count input of the reversible counter 56. The time interval $T_1$ is coded by the number N stored in the reversible counter 56:

$$N = T_1 f_3 \tag{12}$$

where $f_3$ is the repetition frequency of the count pulses.

Figure 6D:
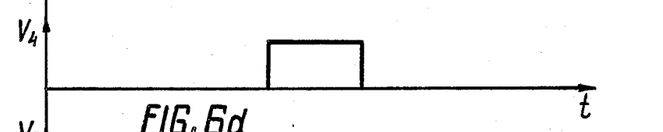
Figure 6E:
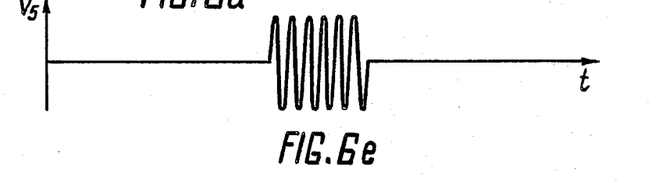

A regular clock pulse $V_1$ (FIG. 6a) transfers the trigger 52 (FIG. 2) to a new state, in which a high potential is produced at its inverse output 55. The leading edge of this voltage pulse sets the trigger 54 of the measuring channel to the "one" state (FIG. 6d). In this case the switching circuit 13 (FIG. 3) of the measuring circuit is rendered conductive and the measuring coil 47 is inserted in the oscillatory circuit of the LC self-excited oscillator built around transistors 59, 60. The LC self-excited oscillator generates a measuring wave train $V_5$ (FIG. 6e). At the same time, the switching circuit 58 (FIG. 2) is rendered conductive and counting pulses are applied to the inverse count input of the reversible counter 56. The inverse counting is effected until the previously recorded number N is read. Since the reading of this number is effected by pulses of the same repetition frequency $f_3$ as during the recording, the duration of reading the number N is equal to $T_1$ (12). After the process of reading is over, the counter 56 produces a command for resetting the trigger 54 to the "zero" state. (FIG. 6d). Thus, a pulse having a length $T_1$ is generated at the "one" output of the trigger 54 (FIG. 2). This length is equal to the duration $T_2$ of the measuring wave train (FIG. 6e).

$$T_1 = T_2 \tag{13}$$

Equation (13) shows that the duration of the measuring wave train under the effect of destabilizing factors obeys the same law as the duration of the correcting wave train. This provides correction of the measuring errors.

To prove that, assume that during the calibration of the system, by some value, the mass of solid particles fed into the sedimentation cylinder 2 correspond to a definite value of the frequency $f_{02}$ of the measuring channel. Equation (13) implies that the number $N_{02}$ of waves in the measuring wave train is given by the expression $$N_{02} = f_{02}T_{02} = f_{02}T_{01} \tag{14}$$

Then assume that with a constant mass of solid particles in the suspended matter under the effect of mechanical or electrical destabilizing factors the frequency of the measuring channel becomes to be equal to $$f_2 = f_{02} + \Delta f_2 \tag{15}$$

The number of waves in the measuring wave train is found as $$N_2 = (f_{02} + \Delta f_2)T_1 = f_{02}T_1\left(1 + \frac{\Delta f_2}{f_{02}}\right) \tag{16}$$

By substituting the value $T_1$ (from (11) into (16), we obtain $$N_2 = \frac{f_{02}T_{01}\left(1 + \frac{\Delta f_2}{f_{02}}\right)}{1 + \frac{\Delta f_1}{f_{01}}} \tag{17}$$

Because of the fact that the same LC self-excited oscillator is used and the relative frequency variations are equal to $$\frac{\Delta f_2}{f_{02}} = \frac{\Delta f_1}{f_{01}}, \quad (18)$$

from (17) it follows that $$N_2 = N_{02} \quad (19)$$

Thus it is proved that in the claimed automatic system the effect of the destabilizing factors had not affected the readings with a constant value of the physical parameter being measured.

The control device 35 (FIG. 1) produces a set of commands providing the preparation of the system to operation, conduction of the analysis and processing of the measurement data. The reference signal generator 72 (FIG. 4) produces an initial train of pulses, by means of which a counter 74 and a decoder 75 connected in series produce a set of commands for controlling the actuators 28 (FIG. 1), 31, 32, 33, 34. The timer 73 (FIG. 4) produces time markers for recording the readings for calculation of the percentage of the mass of solid particles of the sizes being analyzed.

Figure 7A:
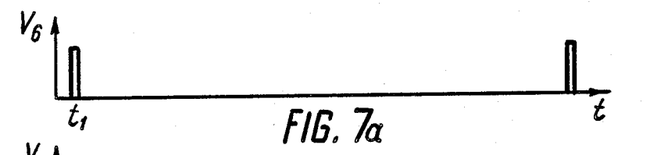
FIGS. 7a–7e are time diagrams illustrating the succession of control signals sent to the actuators.
Figure 7B:
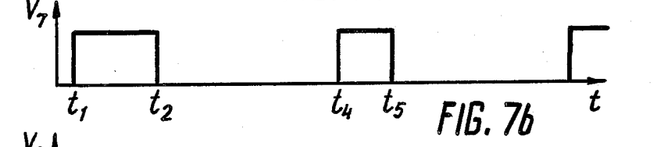

In a practical embodiment of the invention, the sampling of slurry for the material size analysis was carried out from a flotation process flow by its multiple crossing by a knife sampler (not shown). By a command "slurry supply" at the instant $t_1$ (FIG. 7a) the slurry was transported by compressed air through a slurry pipeline (not shown) to the device 23 (FIG. 1). Simultaneously, at the instant $t_1$ (FIG. 7b) the actuator 28 (FIG. 2) was switched on and the slurry being fed into the device 23 was stirred during a time interval ($t_1, t_2$) (FIG. 7b). The volume of the supplied slurry was equal to about 2 liters.

Figures 7C, 7D:
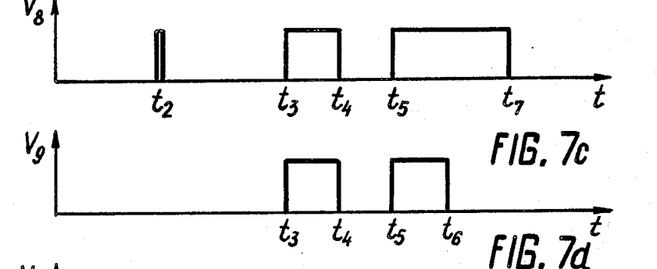

At the instant $t_2$ (FIG. 7c) the valve 30 (FIG. 1) was opened and the sample is fed into the sedimentation cylinder 2. The duration of the input pulse was 0.4 s. The volume of the sample fed into the sedimentation cylinder 2 was equal to about 150 ml. The analysis of the sizes of the taken sample was effected from the instant $t_2$ to the instant $t_3$. After the analysis has been done, at the instant $t_3$ (FIG. 7c, d) the valves 49 (FIG. 1) and 30 were opened simultaneously. During the interval ($t_3, t_4$) the slurry was drained from the device 23 and the waste suspended matter was removed from the sedimentation cylinder 2.

Figure 7E:
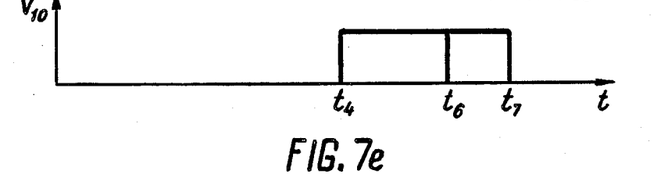

At the instant $t_4$ (FIG. 7c, d) both valves 49, 30 were closed, the actuators 28 and 31 (FIG. 1) are switched on and a liquid was fed into the device 23. The washing of this device was carried out during the time interval ($t_4, t_5$) (FIG. 7b). At the instant $t_5$ both valves 49 (FIG. 1), 30 were opened again and the liquid was drained from the device 23; then during the time interval ($t_5, t_6$) (FIG. 7d) the device 23 (FIG. 1) and the sedimentation cylinder 2 were washed running water. At the instant $t_6$ (FIG. 7d) the valve 49 of the sedimentation cylinder 2 was closed while the valve 30 of the device 23 was still open. During the time interval ($t_6, t_7$) (FIG. 7e) the sedimentation cylinder 2 was with liquid (FIG. 1). At the instant $t_7$ (FIG. 7e) the supply of the liquid was stopped and the valve 30 of the device 23 was closed.

The automatic system was prepared for conduction of a regulator analysis of the sizes of a ground material.

The claimed automatic system has a higher accuracy of analysis of sizes of materials in the process slurry flow due to the following improvements:

(1) higher representability of the sample sampled from the process flow for analysis;

(2) a reduced methodical error of the analysis by providing conditions for free settling of particles in the sedimentation cylinder;

(3) elimination of the destabilizing factors of mechanical and electrical character on the result of the analysis; and (4) use of an improved differential system.

Good representation of the sample is obtained due to the use of the device 23 making it possible to use for the analysis of the sizes of a considerable volume of the slurry representing the process flow being measured. At the same time, careful stirring of the slurry provides its uniform density along the height of the device 23 and this provides good representation of the sample being introduced into the sedimentation cylinder 2 as a small portion of the slurry. Thus conditions for free settling of solid particles are provided.

The accuracy of the analysis is increased due to the fact that the measuring and correcting channels are identical, with respect to the action of destabilizing factors and efficient suppression of the effect of the destabilizing factors on the process of analysis.

The use of an LC self-excited oscillator with a frequency output in combination with an error correction device having no units producing analog signals significantly improves the noise immunity of the system as a whole and makes it suitable for performing high-accuracy industrial analyses of the granulometric composition of ground materials.

What is claimed is:

1. An automatic system for analysis of particle size distribution of a ground material, comprising
   a sampler for sampling and delivering a slurry containing ground material particles;
   a supply of liquid whose density is lower than that of said ground material;
   a measuring tube having lower and upper ends;
   a correcting tube having lower and upper ends;
   a sedimentation cylinder having a side surface, said sedimentation cylinder being filled with said liquid and fluidly communicating with measuring tube and correcting tube, said tubes being spaced from each other along the height of said sedimentation cylinder and connected at said lower ends to said side surface of said sedimentation cylinder for communicating the two lower ends of said tubes and said sedimentation cylinder; said upper ends of said measuring and correcting tubes being located at the same upper level with respect to said sedimentation cylinder;
   a funnel having a widening part and a narrow outlet located inside said sedimentation cylinder coaxially therewith, said narrow outlet having an end face, said lower end of said measuring tube being located below said end face of said narrow outlet of said funnel;
   an actuator for remote control of said supply of said liquid into said sedimentation cylinder;
   an actuator for remote control of sampling and delivery of slurry;
   an actuator for remote control of stirring of said slurry;

an actuator for remote control of introduction of said sample into said sedimentation cylinder;

an actuator for remote control of removal of waste suspended matter from said sedimentation cylinder;

a control device having control outputs connected to said remote control actuators, timer outputs, count-pulse and clock-pulse outputs;

a receiving device for reception and stirring of said slurry and supplying a small part of the slurry into said sedimentation cylinder, said receiving device being connected to said sampler and to said widening part of said funnel, and includes a cylindrical tank, a pressure housing installed coaxially inside said cylindrical tank, a propeller and a shaft of said propeller, said propeller being disposed inside said pressure housing and mounted on said shaft;

a differential circuit which measures the mass of the ground material in the slurry, which has not settled in said sedimentation cylinder at any time of the analysis, and includes:

a measuring liquid level sensing element connected to said upper end of said measuring tube, a correcting liquid level sensing element connected to said upper end of said correcting tube, first and second switching elements having control inputs, and a converter for converting a liquid level into an electric signal, connected through said first and second switching elements to said measuring and correcting liquid level sensing elements, said converter having a data output and a control input;

an automatic error correction device having a data input connected to said data output of said converter and first and second outputs connected to said control inputs of said second and first switching elements respectively and to said control input of said converter, and further having a count-pulse input and a clock-pulse input connected, respectively, to said count-pulse output and to said clock-pulse output of said control device;

a unit for data processing and display of information on the weight percent of the size fractions, said unit for data processing and display having a data input presenting information on the percentage of solid particles in said ground material sizes being analyzed which is connected to said data output of said converter and having control inputs connected to said timer outputs of said control device.

2. An automatic system as claimed in claim 1, in which said automatic error correction device comprises:

a scaler having an input connected to said data output of said converter and an output;

a first trigger having first and second inputs and an output, said first input of said first trigger being connected to said output of said scaler, said output of said first trigger being said first output of said automatic error correction device;

a counting trigger having an inverse output and an input connected to said clock-pulse output of said control device, and a direct output connected to said "zero" second input of said first trigger;

a second trigger having first and second inputs and an output being said second output of said automatic error correction device, said first input of said second trigger being connected to said inverse output of said counting trigger;

a reversible counter having summing and subtracting inputs, and an output;

a direct count switching circuit having a control input and an output and a signal input;

an inverse count switching circuit having a control input and an output and a signal input, said signal inputs of said direct and inverse count switching circuits being connected to said count-pulse output of said control device, said output of said direct count switching circuit being connected to said summing input of said reversible counter, said output of said inverse count switching circuit being connected to said subtracting input of said reversible counter, said output of said reversible counter being connected to said second input of said second trigger, and said control inputs of said direct and inverse count switching circuits being connected to said outputs of said first and second triggers respectively.

3. An automatic system as claimed in claim 1, in which said sedimentation cylinder has a longitudinal axis and a side surface, said lower end of said correcting tube having a lower point of connection with said side surface of said sedimentation cylinder, said end face of said narrow outlet of said funnel being located in a plane perpendicular to said longitudinal axis of said sedimentation cylinder and extending through said lower point of connection of said lower end of said correcting tube with said side surface of said sedimentation cylinder.

* * * * *